United States Patent
Salazar et al.

(10) Patent No.: US 10,519,363 B2
(45) Date of Patent: Dec. 31, 2019

(54) ULTRA-HIGH SALINITY SURFACTANT FORMULATION

(71) Applicant: Huntsman Petrochemical LLC, The Woodlands, TX (US)

(72) Inventors: Luis C. Salazar, Montgomery, TX (US); David C. Lewis, Conroe, TX (US); Srinivasa Godavarthy, Fort Mill, SC (US)

(73) Assignee: HUNTSMAN Petrochemical LLC, The Woodlands, TX (US)

( * ) Notice: Subject to any disclaimer, the term of this patent is extended or adjusted under 35 U.S.C. 154(b) by 0 days.

(21) Appl. No.: 15/510,459

(22) PCT Filed: Dec. 1, 2015

(86) PCT No.: PCT/US2015/063065
§ 371 (c)(1),
(2) Date: Mar. 10, 2017

(87) PCT Pub. No.: WO2016/099847
PCT Pub. Date: Jun. 23, 2016

(65) Prior Publication Data
US 2017/0283687 A1    Oct. 5, 2017

Related U.S. Application Data

(60) Provisional application No. 62/104,985, filed on Jan. 19, 2015, provisional application No. 62/092,441, filed on Dec. 16, 2014.

(51) Int. Cl.
| | | |
|---|---|---|
| *C09K 8/584* | (2006.01) | |
| *C07C 305/10* | (2006.01) | |
| *C07C 309/10* | (2006.01) | |
| *C08G 65/26* | (2006.01) | |
| *C08G 65/334* | (2006.01) | |
| *E21B 43/16* | (2006.01) | |

(52) U.S. Cl.
CPC ............ *C09K 8/584* (2013.01); *C07C 305/10* (2013.01); *C07C 309/10* (2013.01); *C08G 65/2609* (2013.01); *C08G 65/3344* (2013.01); *E21B 43/162* (2013.01)

(58) Field of Classification Search
CPC ........ C09K 8/584; C09K 8/594; C09K 8/588; C09K 8/58; C09K 8/94; C09K 2208/32; C09K 8/38; C09K 8/518; C09K 8/52; C09K 8/528; C09K 8/536; C09K 8/54; C09K 8/592; C09K 8/602; C09K 8/607; C09K 8/703; C09K 8/845; C09K 8/88; C09K 8/90; E21B 43/24; E21B 43/164; E21B 43/20; E21B 41/0057; E21B 43/40; E21B 37/06; E21B 43/16; E21B 43/168
See application file for complete search history.

(56) References Cited

U.S. PATENT DOCUMENTS

| | | | | |
|---|---|---|---|---|
| 3,945,437 A | * | 3/1976 | Chiu ..................... | C09K 8/584 166/275 |
| 4,214,999 A | * | 7/1980 | Carlin .................... | C09K 8/584 166/270.1 |
| 4,426,303 A | * | 1/1984 | Nuckels ............. | B01F 17/0085 166/275 |
| 4,757,833 A | | 7/1988 | Danley | |
| 6,348,528 B1 | | 2/2002 | Schlarb et al. | |
| 2009/0078414 A1 | | 3/2009 | Szabo et al. | |
| 2011/0083847 A1 | * | 4/2011 | Bittner .................. | C09K 8/584 166/270.1 |
| 2011/0281779 A1 | * | 11/2011 | Weerasooriya ........ | C09K 8/584 507/254 |
| 2016/0068742 A1 | | 3/2016 | Solastiouk et al. | |

FOREIGN PATENT DOCUMENTS

| WO | 2014193720 A1 | 12/2014 |
|---|---|---|
| WO | WO2014/193720 | * 12/2014 |

* cited by examiner

*Primary Examiner* — Kumar R Bhushan
(74) *Attorney, Agent, or Firm* — Huntsman Petrochemical LLC; Edward Korompai

(57) ABSTRACT

Methods of enhanced oil recovery are disclosed that use compositions including an alkyl polyether anionic surfactant having the general structure $R^1JA$, wherein $R^1$ is a $C_8$-$C_{18}$ primary or secondary radical group, J is a random, block, alternating, or alternating block polyether segment having the structure $[(PO)_x(EO)_y(BO)_z]$, wherein x is 4 to 18, y is 0 to 20, and z is 0 to 5, and A is an anionic group; a co-surfactant having the general structure $(R^2)_q(B)Ph-L-Ph(D)(R^3)_r$, wherein $R^2$ and $R^3$ are each, independently in each instance, a $C_8$-$C_{24}$ linear or branched, primary or secondary alkyl group, B and D are anionic groups, q is 1 to 3, r is 1 to 3, and L is O or $CH_2$; and an alkoxy alcohol.

13 Claims, No Drawings

ULTRA-HIGH SALINITY SURFACTANT FORMULATION

CROSS-REFERENCE TO RELATED APPLICATIONS

This application is the National Phase of International Application PCT/US2015/063065 filed Dec. 1, 2015 which designated the U.S. and which claims priority to U.S. application Ser. No. 62/092,441 filed Dec. 16, 2014 and U.S. application Ser. No. 62/104,985 filed Jan. 19, 2015. The noted applications are incorporated herein by reference.

FIELD

Embodiments of the present disclosure generally relate to an enhanced oil recovery well injection composition, using such a composition for enhanced recovery of an oil well, and methods of making the composition.

BACKGROUND

Enhanced oil recovery is a process wherein an oil well that has suffered a decline in production due to depletion of the resources in the well and loss of reservoir pressure. Candidates for enhanced recovery are typically wells that have been in production for some time so that a significant volume of resources have been extracted from the well. In one type of enhanced oil recovery, a fluid is pumped into a reservoir to contact oil that does not flow at reservoir pressure. The fluid is typically designed to disperse the oil, reduce adhesion of the oil to reservoir structures, or otherwise ease movement of the oil out of the reservoir to the surface.

Many fluids used for enhanced recovery include surfactants and solvents. Such materials are typically blended with water obtained from reservoir structures to form a well injection fluid. The water is usually salty, making mixing with the solvents and surfactants challenging. In wells with high salinity brines, extractors often have to resort to expensive and time-consuming water treatment to reduce salinity and/or mineral hardness of the water. Thus, there is a need for well injection materials that are stable when mixed with high salinity well brines.

DETAILED DESCRIPTION

A composition is disclosed that includes an alkyl polyether anionic surfactant having the general structure $R^1JA$, wherein $R^1$ is a $C_8$-$C_{18}$ primary or secondary radical group, J is a random, block, alternating, or alternating block polyether segment having the structure $[(PO)_x(EO)_y(BO)_z]$, wherein x is 4 to 18, y is 0 to 20, and z is 0 to 5, and A is an anionic group. In this disclosure, "PO" stands for "propylene oxide", "EO" stands for "ethylene oxide", and "BO" stands for "butylene oxide". $R^1$ may be a $C_6$-$C_{20}$ linear, branched, cyclic, or alkyl-cyclic radical, such as a $C_8$-$C_{18}$ primary or secondary radical group, a $C_{10}$-$C_{15}$ primary or secondary radical group, for example a $C_{10}$ radical group or a $C_{13}$ radical group. Alternately, $R^1$ may be a $C_8$-$C_{10}$ alkyl or dialkyl phenol group. The alkyl polyether anionic surfactant generally has a hydrophobic portion that is compatible with a variety of fossil fluids for use in a variety of reservoirs. In some cases, z is 0 and A is $SO_3Na$. A may also be $CH_2CH_2SO_3Na$, $CH_2COONa$, or $PO_3Na$. The surfactant may be a mixture of molecules having different proportions of monomers. For example, if a mixture of alkylene oxides is used to make the polyether portion, local reaction conditions may lead to different combinations of monomers in the individual molecules. In such cases, the surfactant may be described by the formula above, where x, y, and z may have fractional values to represent the "average" molecule of the blend.

The surfactant is typically built by reacting an alcohol with alkylene oxides to form the alkyl polyether, and then reacting the alkyl polyether with an acid to attach the anionic portion. The alcohol may be a $C_8$-$C_{18}$, such as $C_{10}$-$C_{15}$, for example $C_{10}$ or $C_{13}$, primary or secondary, linear or branched, aliphatic or aromatic molecule. In some cases, the alcohol may be a $C_8$-$C_{10}$ alkyl or dialkyl phenol. Mixtures of alcohols may be used.

The alkylene oxide, or a mixture of alkylene oxides, is added to the alcohol(s) to form a reaction mixture that yields the polyether. The alkylene oxides typically include PO, and may include EO, and BO. The molar ratio of alkylene oxides in the surfactant generally follows the molar ratio of alkylene oxides in the reaction mixture. The alkylation reaction may be performed in batch mode or continuous flow. The alkyl polyether portion of the surfactant may be random, block, pseudo-block (i.e. identifiable blocks of different random monomer mixtures), or alternating block, and the blocks may be any length. Blocks may be formed by sequentially adding different alkylene oxides, or mixtures thereof, to the reaction mixture, reacting each mixture to completion, and removing unreacted monomers before adding the next alkylene oxide or mixture. The reactions may be performed in liquid or gas phase. Reaction temperatures can be, but are not limited to, between 120° and 160° C. depending on which oxide is being reacted. At these temperatures reactor vessels capable of handling high pressures may be used. The choice of catalyst will depend on the starting radical and the alkyloxide being used. In some cases, a strong base such as Potassium Hydroxide is used. Other options for catalysts include strong acids and coordination catalysts. The catalyst may be introduced as a solution in a solvent, and the solvent may be removed before the alkyl oxides are introduced into the reactor. Depending on the molecular weight of the alcohol used to start the alkyl polyether portion, between 230 Daltons and 2400 Daltons are added to the alcohol to form an alkyl polyether mixture with alkyl polyether molecules ranging in molecular weight from about 350 to about 2700.

Residual alkylene oxide monomers may be removed, for example by evaporation and stripping with inert gas, for example nitrogen, before attaching the anionic portion. The unreacted monomers, and any solvents used for the reaction or for removing unreacted monomers, may be recycled. An acid is added to the alkyl polyether to attach the anionic portion. The alkyl polyether may be dissolved in a solvent prior to adding the acid, if desired, to facilitate mixing of the reactants, and a solvent may also be included with the acid. Sulfuric acid may be used to add a sulfate anion ($SO_3^-$). Carboxylate, phosphate, and ether sulfonate ions may also be used.

The anionic surfactant may be stabilized as a salt. After reaction with acid to attach the anionic portion, excess acid may be neutralized, and the surfactant stabilized, by adding a base such as sodium hydroxide, or another alkali metal hydroxide such as potassium hydroxide, ammonium hydroxide, or an organic amine. An example of the primary surfactant is a sodium salt of tridecyl alcohol with 8 PO units and 2 EO units added to the average molecule and capped with a sulfate anion.

A co-surfactant may be included in the composition to broaden the range of reservoirs in which the composition is an effective hydrocarbon extraction aid. The co-surfactant may have the general structure $(R^2)_q(B)Ph\text{-}L\text{-}Ph(D)(R^3)_r$, wherein $R^2$ and $R^3$ are each, independently in each instance, a $C_8$-$C_{24}$ linear or branched, primary or secondary alkyl group, B and D are anionic groups, q is 1 to 3, r is 1 to 3, and L is O or $CH_2$. In this disclosure, "Ph" represents a phenyl radical. The co-surfactant may be constructed by any ether-forming reaction, such as acid catalyzed phenol condensation, base catalyzed halide/alcohol elimination (e.g. Williamson reaction), or epoxide ring-opening. In some embodiments, $R^2$ and $R^3$ may be secondary alkyl groups bonded to the phenyl group at the number two carbon atom of the alkyl group. $R^2$ and $R^3$ may be in the meta and/or para positions, relative to L, in some embodiments. B and D may be at any position relative to L and $R^2$, or L and $R^3$, respectively. The co-surfactant may be a disodium dialkylarylsulfonate ether. B and D may each be $SO_3$. The anionic co-surfactant may be stabilized as a salt, for example a sodium or potassium salt.

Examples of co-surfactants that may be used include disodium salts of decyl phenoxybenzenedisulfonic acid, di-decyl phenoxybenzenedisulfonic acid, dodecyl phenoxybenzenedisulfonic acid, di-dodecyl phenoxybenzenedisulfonic acid, and hexyl phenoxybenzenedisulfonic acid.

An alkoxy alcohol may be included in the composition to adjust flow and penetration characteristics of the composition. The alkoxy alcohol may have the general structure $R^4[(PO)_m(EO)_n(BO)_o]OH$, wherein $R^4$ is a $C_1$ to $C_6$ linear, branched, cycloaliphatic, or aromatic hydrocarbyl group, m is 0 to 3, n is 1 to 10, and o is 0 to 3. Examples include alkoxylated n-butanol, i-butanol, and hexanol. An alkoxy alcohol made from n-butanol with two EO groups added is available as SURFONIC® L4-2 from the Performance Products Division of Huntsman, Corp., located in The Woodlands, Tex. Other SURFONIC® products that may be used include SURFONIC® L4-1, SURFONIC® L4-3, SURFONIC® IBA-3, SURFONIC® IBA-5, SURFONIC® L6-6, SURFONIC® L6-8, and SURFONIC® L6-10.

In some cases, a water soluble polymer may be included in the composition to improve the sweep efficiency of the composition as it moves through the reservoir. The polymer prevents viscous fingering of the composition as it moves through the reservoir. Partially hydrogenated polyacrylamide polymers like the Flopaam series available from SNF are useful in this application. The polymers may also include special comonomers like AMPS that help impart extra brine and hardness tolerance.

The compositions described above may be added to well brines having ultra-high salinity. A composition such as that described herein may be mixed with a well brine to form an injection brine. A concentration of the primary surfactant in the injection brine may be between about 0.5 wt % and about 5 wt %, for example about 1 wt %. The co-surfactant is typically used in a weight ratio to the primary surfactant of about 0.3 to about 0.5, for example from about 0.375 to about 0.438. The co-surfactant may be use in a weight ratio to the primary surfactant of about 0.2 to 2.0. The amounts of co-surfactant and co-surfactant may depend on salinity and temperature of the reservoir.

The components described above may be included in a water concentrate containing 75% or more of the active ingredients described above and up to 25% water, for example 25 to 50% active ingredients with the balance being water.

The composition above is generally useful when blended in appropriate amounts with water surfaced from oil wells. The water may be native to the reservoir, or produced water that has resulted from water flooding reservoir may be used. Such produced water is typically a brine solution with 100,000 ppm total dissolved solids or more. In some cases, the compositions described herein may be used with brines having up to 200,000 ppm total dissolved solids. Typical injection water used for water flooding oil reservoirs in the Permian Basin of Texas, for example, have salinities in the range of 120,000 to 200,000 ppm of dissolved solids.

A method of forming an enhanced oil recovery well injection composition is also disclosed, including forming a concentrate by mixing a water solution of a surfactant having the general structure $R^1JA$ defined above, with a co-surfactant having the general structure $(R^2)_q(B)Ph\text{-}L\text{-}Ph(D)(R^3)_r$ defined above, and an alkoxy alcohol as described above; and forming an enhanced oil recovery well injection composition by mixing the concentrate with untreated well brine having total dissolved solids of about 100,000 ppm or more and hardness of about 4,000 ppm or more.

The water solution of the surfactant may be formed by mixing an alkyl polyether alcohol having the general formula $R^1JOH$ with sulfuric acid to form an anionic surfactant and neutralizing with sodium hydroxide, or another alkali metal hydroxide such as potassium hydroxide, ammonium hydroxide, an organic amine. The co-surfactants and alkoxy alcohols described above may be added in a mixed vessel or in continuous flow using a mixing insert such as a static mixer. As above, mixtures of surfactants, co-surfactants, and alkoxy alcohols may be used, and a water soluble polymer may be added. The untreated well brine is typically pumped out of the well into a mixing vessel, or a tank to be fed through an in-line mixer, as described above. The finished injection composition may be stored in a tank at the well site, and may be heated or cooled to a desired temperature before injection into the well. Additionally, the injection composition, or any component thereof, may be blended off-site and transported to the well site for injection. For example, a concentrate made from a water solution of the surfactants described above, the co-surfactants described above, and the alkoxy alcohols described above, may be obtained and mixed at the well site with the untreated well brine.

An exemplary composition contains a surfactant having the structure of formula (1):

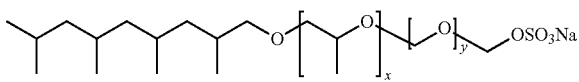

(1)

where x is 4 to 18, for example 8, and y is 0 to 20, for example 0.1. A fractional value here indicates that the composition contains molecules of the structure above where y is zero, and molecules of the structure above where y is non-zero. The exemplary composition also has a co-surfactant with the structure of formula (2):

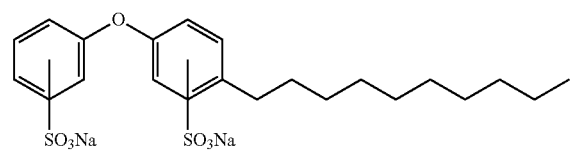

(2)

along with a co-surfactant that is an ethoxylate of butanol having the structure of formula (3):

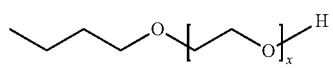

(3)

where x is 0 to 6, and has an average value of about 2. The above components are added in the general proportions described above.

Results of using compositions as described herein mixed with some actual reservoir samples are shown below. Fluid samples from three different fields were obtained. The samples all had ultra-high salinity injection waters, and the reservoirs had moderate temperature. In some cases, only a primary and co-surfactant were used. In other cases a co-surfactant was also used. For each mixture, the Windsor phase type was recorded. Windsor phase I type mixtures feature an oil-in-water microemulsion in the aqueous phase. Windsor phase II type mixtures feature a water-in-oil microemulsion in the oil phase. These types indicate that interfacial surface tension is too high for good enhance oil recovery results. Windsor phase III type features a third phase between the oil and water phases that has dissolved hydrocarbons. This type indicates interfacial surface tension is low enough for good results in enhanced oil recovery processes.

TABLE 1

Field 1
Reservoir Temperature 30° C., Total Dissolved Solids 170,000 ppm

| | Amount in Injection Brine, wt % | | Windsor |
|---|---|---|---|
| Mixture # | Primary Surfactant | Co-Surfactant | Phase in Mixture |
| 1 | 1 | 0.250 | II |
| 2 | 1 | 0.375 | III |
| 3 | 1 | 0.438 | III |
| 4 | 1 | 0.500 | I |
| 5 | 1 | 0.563 | I |
| 6 | 1 | 0.625 | I |

TABLE 2

Field 1
Reservoir Temperature 30° C., Total Dissolved Solids 170,000 ppm

| | Amount in Injection Brine, wt % | | | Windsor |
|---|---|---|---|---|
| Mixture # | Primary Surfactant | Co-Surfactant | Co-surfactant | Phase In Mixture |
| 1 | 1 | 0.360 | 0.200 | III |
| 2 | 1 | 0.360 | 0.400 | III |
| 3 | 1 | 0.360 | 0.600 | III |
| 4 | 1 | 0.360 | 0.800 | III |
| 5 | 1 | 0.450 | 0.200 | I |
| 6 | 1 | 0.450 | 0.400 | I |
| 7 | 1 | 0.450 | 0.600 | I |
| 8 | 1 | 0.450 | 0.800 | I |

TABLE 3

Field 2
Reservoir Temperature 38° C., Total Dissolved Solids 120,000 ppm

| | Amount in Injection Brine, wt % | | | Windsor |
|---|---|---|---|---|
| Mixture # | Primary Surfactant | Co-Surfactant | Co-surfactant | Phase in Mixture |
| 1 | 1 | 0.300 | 0.300 | III |
| 2 | 1 | 0.400 | 0.300 | III |
| 3 | 1 | 0.500 | 0.300 | III |
| 4 | 1 | 0.300 | 0.400 | III |
| 5 | 1 | 0.400 | 0.400 | III |
| 6 | 1 | 0.500 | 0.400 | III |
| 7 | 1 | 0.300 | 0.500 | III |
| 8 | 1 | 0.400 | 0.500 | III |
| 9 | 1 | 0.500 | 0.500 | III |

TABLE 4

Field 3
Reservoir Temperature 38° C., Total Dissolved Solids 120,000 ppm

| | Amount in Injection Brine, wt % | | | Windsor |
|---|---|---|---|---|
| Mixture # | Primary Surfactant | Co-Surfactant | Co-surfactant | Phase in Mixture |
| 1 | 1 | 0.300 | 0.500 | III |
| 2 | 1 | 0.300 | 1.000 | III |
| 3 | 1 | 0.300 | 1.250 | III |
| 4 | 1 | 0.300 | 1.500 | III |
| 5 | 1 | 0.300 | 2.000 | III |

While the foregoing is directed to embodiments of the present disclosure, other and further embodiments of the disclosure may be devised without departing from the basic scope thereof, and the scope thereof is determined by the claims that follow.

What is claimed is:

1. A composition, comprising:
   a) greater than 75% of active ingredients comprising:
      an alkyl polyether anionic surfactant having the general structure $R^1JA$, wherein $R^1$ is a $C_8$-$C_{18}$ primary or secondary radical group, J is a random, block, alternating, or alternating block polyether segment having the structure $[(PO)_x(EO)_y(BO)_z]$, wherein x is 4 to 18, y is 0 to 20, and z is 0 to 5, and A is an anionic group;
      a co-surfactant having the general structure $(R^2)_q(B)Ph$-$L$-$Ph(D)(R^3)_r$, wherein $R^2$ and $R^3$ are each, independently in each instance, a $C_8$-$C_{24}$ linear or branched, primary or secondary alkyl group, B and D are anionic groups, q is 1 to 3, r is 1 to 3, and L is O or $CH_2$; and
      an alkoxy alcohol; and
   b) up to 25% of water.

2. The composition of claim 1, wherein the co-surfactant is a dialkylarylsulfonate ether.

3. The composition of claim 2, wherein the alkoxy alcohol has the general structure $R^4[(PO)_m(EO)_n(BO)_o]OH$, wherein $R^4$ is a $C_1$ to $C_6$ linear, branched, cycloaliphatic, or aromatic hydrocarbyl group, m is 0 to 3, n is 1 to 10, and o is 0 to 3.

4. The composition of claim 1, wherein z is 0, L is O, and A is $SO_3Na$, $CH2CH2SO3Na$, $CH2COONa$, or $PO3Na$.

5. The composition of claim 4, wherein B and D are each $SO_3Na$, and the alkoxy alcohol has the general structure $R^4[(PO)_m(EO)_n(BO)_o]OH$, $R^4$ is a $C_1$ to $C_6$ linear, branched, cycloaliphatic, or aromatic hydrocarbyl group, m is 0 to 3, n is 1 to 10, and o is 0 to 3.

6. The composition of claim 5, wherein o is 0, m is 0, and $R^4$ is a linear or branched $C_4$ alkyl group.

7. The composition of claim 6, wherein $R^2$ and $R^3$ are each, independently in each instance, a $C_8$ to $C_{12}$ linear primary alkyl group, and q and r are each 1.

8. The composition of claim 7, wherein $R^1$ is a $C_{10}$ to $C_{15}$ primary linear alkyl group.

9. The composition of claim 8, wherein J is a block polyether segment.

10. The composition of claim 9, further comprising a water soluble polymer.

11. The composition of claim 1, further comprising a salt water solution having at least about 100,000 ppm total dissolved solids and at least about 4,000 ppm of alkaline earth ions.

12. The composition of claim 4, further comprising a salt water solution having at least about 100,000 ppm total dissolved solids and at least about 4,000 ppm of alkaline earth ions.

13. The composition of claim 9, further comprising a salt water solution having at least about 100,000 ppm total dissolved solids and at least about 4,000 ppm of alkaline earth ions.

\* \* \* \* \*